United States Patent [19]

Sulzer et al.

[11] Patent Number: 4,568,779

[45] Date of Patent: Feb. 4, 1986

[54] POLYPHOSPHAZENE PROCESS

[75] Inventors: Gerald M. Sulzer; R. Woodrow Wilson, Jr., both of Baton Rouge, La.

[73] Assignee: Ethyl Corporation, Richmond, Va.

[21] Appl. No.: 601,506

[22] Filed: Apr. 18, 1984

[51] Int. Cl.$^4$ ............ C07C 31/34; C07C 31/36; C07C 31/38
[52] U.S. Cl. ............ 568/842; 568/841; 568/844
[58] Field of Search ............ 568/841, 842, 844, 851

[56] References Cited

U.S. PATENT DOCUMENTS 3,844,983 10/1974 Reynard.
4,150,244 4/1979 Knorre et al. ............ 568/851

FOREIGN PATENT DOCUMENTS 517360 10/1955 Canada ............ 568/851

OTHER PUBLICATIONS

Pattison et al., J. Org. Chem. 21, No. 7, 1956, pp. 739–742.

Primary Examiner—Howard T. Mars
Attorney, Agent, or Firm—Donald L. Johnson; John F. Sieberth; Joseph D. Odenweller

[57] ABSTRACT

A process for making an alkali metal alkoxide (e.g. sodium alkoxide) of a halogen-substituted alcohol (e.g. fluorine-substituted alcohols) by dispersing an alkali metal (e.g. sodium) in a cycloalkane (e.g. cyclohexane) and adding the resultant dispersion to an ether (e.g. THF) solution of a halogen-substituted alcohol. The resultant alkali metal haloalkoxide solution can be reacted with a phosphonitrilic chloride polymer to introduce haloalkoxide substituents.

11 Claims, No Drawings

POLYPHOSPHAZENE PROCESS

BACKGROUND OF THE INVENTION

Haloalkoxide-substituted phosphazene polymers are useful in many applications because of their flame resistance, low temperature flex properties and high temperature stability. Of these, most interest has been in the fluoroalkoxide-substituted polyphosphazene. Such compositions are disclosed in U.S. Pat. No. 3,515,688 and U.S. Pat. No. 3,700,629. Other fluoroalkoxides-substituted phosphazene polymers are disclosed in U.S. Pat. No. 3,702,833, U.S. Pat. No. 3,732,175, U.S. Pat. No. 3,838,073, U.S. Pat. No. 3,844,983, U.S. Pat. No. 3,888,799, U.S. Pat. No. 3,888,800, U.S. Pat. No. 3,896,058, U.S. Pat. No. 3,943,088, U.S. Pat. No. 3,945,966, U.S. Pat. No. 3,948,820, U.S. Pat. No. 3,970,533, U.S. Pat. No. 3,972,841, U.S. Pat. No. 4,000,166, all of which are incorporated herein by reference for their disclosure of the prior methods of making alkaline metal fluoroalkoxides and the use of such fluoroalkoxides in preparing polyphosphazene polymers and the utility of such polyphosphazene polymers.

In U.S. Pat. No. 3,515,688, the sodium fluoroalkoxide used to make the fluoroalkoxide-substituted phosphazene polymers was prepared by reacting metallic sodium directly with the fluorine-substituted alcohol. Pieces of metallic sodium, which were cut and weighed under dried benzene, were added directly to the fluorine-substituted alcohol and the mixture stirred overnight following which it was refluxed to complete the reaction. A hazard associated with a process carried out in this manner is that the metallic sodium in addition to reacting with the alcohol hydroxyl groups can also react with the halogen bonded to the alcohol. Such reactions can become very exothermic and lead to eruption of the reaction contents from the reaction vessel and can ignite. Attempts to prepare sodium alkoxides of fluorine-substituted alcohols using sodium dispersed in tetrahydrofuran (THF) were not successful because the sodium dispersion initially made in THF tended to coalesce.

SUMMARY OF THE INVENTION

It has now been discovered that sodium dispersions made in a cycloalkane such as cyclohexane retain their dispersed state and when added in a controlled manner to a fluorine-substituted alcohol react rapidly with the alcoholic hydroxyl group without accumulating large amounts of unreacted sodium which could lead to the hazard referred to above. The sodium fluoroalkoxide prepared in this manner reacts very efficiently with phosphonitrilic chloride polymers thereby replacing the chlorine atoms with fluoroalkoxide groups.

DESCRIPTION OF PREFERRED EMBODIMENTS

A preferred embodiment of the invention is a process for making a sodium alkoxide of a halogen-substituted alcohol without excessive reaction of sodium with the halogen substituent, said process comprising
(a) dispersing molten metallic sodium in a cycloalkane hydrocarbon containing about 5-8 carbon atoms at a pressure high enough to maintain said cycloalkane hydrocarbon in the liquid phase above the melting temperature of sodium;
(b) cooling the resultant dispersion to a temperature below the melting point of sodium; and
(c) adding about preferably 0.9-1.0 equivalents of the resultant sodium dispersion to a solution of 1 equivalent of a halogen-substituted alcohol in an ether solvent at a temperature of about −30° C. up to reflux, said equivalents being based on the hydroxyl content of said halogen-substituted alcohol.

Preferred cycloalkane useful in the process are those containing about 5-8 carbon atoms such as cyclopentane, cyclohexane, cycloheptane and cyclooctane. The cycloalkane ring may be substituted with alkyl groups such as methyl, ethyl, propyl and the like. The preferred cycloalkane hydrocarbon is cyclohexane.

Alkali metals that can be used in the process include both sodium and potassium. Of these, sodium is most preferred because of its ready availability and low cost. The amount of sodium in the dispersion can vary over a wide range. A preferred concentration is from about 20-50 weight percent sodium in the resultant sodium dispersion. A more preferred sodium concentration is from about 30 to 40 weight percent.

The dispersion is prepared by adding metallic sodium to the cycloalkane hydrocarbon and heating the mixture to a temperature above the melting point of sodium and maintaining at this temperature until the sodium becomes molten. Sodium melts at about 97.5° C. which is above the normal boiling point of cyclopentane and cyclohexane. When the temperature used to make the dispersion is above the normal boiling point of the cycloalkane dispersion medium pressure equipment must be used to prepare the dispersion. Only modest pressures are encountered. For example, using cyclohexane at 105° C. resulted in a pressure of 14 psig.

Optionally, the sodium can be pre-melted and added to the hot cycloalkane in order to reduce processing time.

The sodium used in the process should be cleaned of oxides and hydroxides which frequently form on the surface of metallic sodium. The dispersing temperature is preferably about 105°-120° C. although temperatures as low as 100° C. can be used. The dispersion is then formed by vigorously agitating the mixture using a high shear dispersing agitator such as a conventional turbine type dispersing head. Such dispersing heads are used at very high RPM such that the tip speed of the agitator is in the vicinity of 45-90 feet per second.

Dispersing agents can be used in making the dispersions although they are generally not necessary. Useful dispersing agents include fatty acids such as oleic acid which forms sodium oleate in the dispersion. Preferably the use of a dispersing agent should be avoided because it tends to introduce an impurity into the reaction system when the alkali metal haloalkoxide is reacted with the phosphonitrilic chloride polymer. Impurities are generally detrimental to the properties of the substituted polymer and elaborate purification methods become necessary to eliminate impurities.

Halogen-substituted alcohols which can be reacted to form sodium alkoxides according to the present process include any halogen-substituted alcohol and can contain up to 20 or more carbon atoms and 41 or more halogen atoms. Halogen substituents include chlorine, fluorine, bromine and iodine. Examples of such halogen-substituted alcohols are trifluoromethanol, trichloromethanol, 2-chloro-ethanol, 2,2-dichloroethanol, 2,2-difluoroethanol, 2,2-dibromoethanol, 2,2,2-trifluoroethanol, 2,2,2-trichloroethanol, 2,3-dibromopropanol, 2,3-diiodopropanol, 2,2,3,3,3-pentafluoropropanol, 6,6-dichlorohexanol, 7,8-dibromooctadecanol, 7,8-difluorooctadecanol, 8,9-diiodoeicosanol and the like.

In a more preferred embodiment, the halogen-substituted alcohol is a fluorine-substituted alcohol. In a still more preferred embodiment, the fluorine-substituted alcohol is a mixture of (a) trifluoroethanol and (b) a telomer alcohol having the general formula $X(CF_2)_pCH_2OH$ wherein X is hydrogen or fluorine and p is an even integer from 2 to about 12 and mixtures of such telomer alcohols.

Preferably the mixture contains (a) about 30–70 wt% trifluoroethanol and (b) about 70–30 wt% of the telomer alcohol.

The alcohol reactant can include halogen-free alcohols as well as phenols when the product is desired to contain alkoxides or aryloxides of such alcohols and/or phenols. However, in order for the process to be beneficial the alcohol reactant should contain a substantial amount of halogen-substituted alcohol. For example, alcohol mixtures containing 10 wt% or more halogen-substituted alcohols can benefit from the present process.

The haloalcohol is dissolved in an ether solvent. A wide range of ethers can be used provided they are substantially inert under the reaction conditions. It is highly preferred that the ether solvent also be capable of dissolving the haloalkoxide-substituted polyphosphazene formed when the sodium haloalkoxide is reacted with phosphonitrilic chloride polymer. Useful solvents are diethyl ether, ethyl butyl ether, dibutyl ether, dioxane, dimethoxy ethane, diethoxy ethane, dimethyl ether of diethylene glycol, dibutoxy ethane, dibutyl ether of diethylene glycol. Most work has been carried out using tetrahydrofuran (THF) as the haloalcohol solvent.

The amount of ether solvent should be an amount which will dissolve at least a major portion of the sodium haloalkoxide formed in the reaction. More preferably the amount is sufficient to dissolve substantially all of the sodium haloalkoxide formed in the reaction. The amount required will vary with what ether is selected and what haloalkoxide is prepared. The requirement amount can be determined experimentally with very little effort. A useful range in which to test is about 300–5000 parts by weight ether for each 100 parts of haloalcohol. A more preferred range is about 350–1000 parts of ether solvent per 100 parts haloalcohol. When making a sodium fluoroalkoxide using the preferred telomer alcohols good results have been achieved with about 300–400 parts THF per 100 parts telomer alcohol.

The sodium dispersion is added to the halogen-substituted alcohol at a rate such that there is not a large amount of unreacted sodium in the halogen-substituted alcohol at any time. The rate of sodium reacting with the alcohol hydroxyl to form alkoxide can be followed by measuring hydrogen evolution. Generally, good results have been obtained by limiting sodium feed such that there is less than 0.02 wt% unreacted sodium in the reaction mixture at any time.

The temperature of the reaction mixture need not be raised. Preferably the reaction temperature is maintained at about −20° to +30° C. Excellent results with no noticeable halogen reaction have been obtained at about −10° to +20° C. The preferred reaction temperature is about −5° up to about 10° C.

The amount of sodium dispersion added to the halogen-substituted alcohol should be an amount which is sufficient to react with most of the alcohol hydroxyl groups. A preferred amount is about 0.8–1.5 equivalent of sodium per each equivalent of alcohol hydroxyl. A more preferred range is about 0.9–1.0 equivalents of sodium per alcohol hydroxyl equivalent. Most preferably about one equivalent of sodium is added for each equivalent of alcohol hydroxyl.

Addition time for the sodium dispersion is generally about ten minutes up to about eight hours. The reaction mixture is stirred during this time under an inert atmosphere such as nitrogen. After completion of the addition, the mixture is stirred for a short period up to about two hours. Any unreacted sodium remaining at this time can be removed by filtration. The following examples show how the process is conducted.

EXAMPLE 1

In a pressure resistant dispersion vessel fitted with a high speed turbine type dispersing head was placed 300 parts of cyclohexane. The vessel was purged with nitrogen and 200 parts of clean sodium pieces were dropped into the cyclohexane. The dispersion vessel was sealed and heated to 105° C. at which time pressure had increased to about 14 psig. The high speed agitator was started and run at about 14,000–16,000 rpm for 13 minutes to disperse the molten sodium. At this time, the agitator was stopped and the mixture permitted to slowly cool to a temperature below the melting point of sodium resulting in a stable sodium dispersion in cyclohexane.

EXAMPLE 2

In the dispersing vessel of Example 1 was placed 255 grams of cyclohexane and 170 grams of sodium pieces. The vessel was purged with nitrogen and sealed and heated to 110° C. The high shear agitator was started and run at 9,600 rpms. The dispersion was not completely stable so agitator speed was increased to 11,500 rpm and run at this speed for 20 minutes. Agitation was stopped and the dispersion cooled to about 60° C. Particle size was too large for easy discharge through a one-quarter inch tubing so the mixture was again heated to about 110° C. The high shear agitator was started and run at 13,300 rpms for 20 minutes. The agitator was stopped and the dispersion allowed to cool to 40° C. The particle size was very small and the appearance of the dispersion was good, and the material easily transferred through a clean ¼" tube.

EXAMPLE 3

In a reaction vessel fitted with stirrer and thermometer was placed 1490 g tetrahydrofuran, 182 g 2,2,2-trifluoroethanol and 191 g of telomer alcohol in which X is fluorine, p is 2–8 and has an average value of about 4. This was stirred under nitrogen and over a period of 3 hours. 60 g of the sodium dispersion made in Example 1 was added while maintaining the temperature in the range of −30° C. to 4° C. The reaction went smoothly giving a solids-free sodium fluroalkoxide product.

This example was repeated using 110 minute sodium dispersion feed time with excellent results.

The alkali metal haloalkoxides made by the process are used to insert haloalkoxide groups on phosphonitrilic chloride polymers (chloropolymers). Chloropolymers are well known compositions and come in a wide range of molecular weights. At one extreme are the low molecular weight cyclic chloropolymers containing about 3–7 $(PNCl_2)$ units such as phosphonitrilic chloride trimer and tetramer made by the reaction of $PCl_5$ and $NH_4Cl$ in approximately equal mole amounts in a solvent such as monochlorobenzene. Slightly higher molecular weight oligomer products can be made by the same general reaction using a molar excess of $PCl_5$. These oligomers usually contain about 3-9 $(PNCl_2)$ units.

The cyclic polymers can be converted to high molecular weight chloropolymers by heating the purified cyclic chloropolymer to temperatures in the range of about 220°-275° C. The low molecular weight oligomers can be converted to high molecular weight chloropolymers by heating with $NH_4Cl$ at a temperature of about 130°-200° C. as described in U.S. Pat. No. 4,374,815.

Although the sodium haloalkoxides made by the present process can be reacted with any chloropolymer to introduce haloalkoxide group, it is preferred that the chloropolymer contain at least about 10 $(PNCl_2)$ units. More preferably, the chloropolymer is a high molecular weight substantially linear chloropolymer containing over 100 $(PNCl_2)$ units and most preferably over 1,000 such units.

The haloalkoxide groups are introduced into the chloropolymer by dissolving the chloropolymer in an inert solvent and then adding the ether solution of the haloalkoxide. Suitable solvents for the chloropolymer are ethers, aromatics, cycloaliphatics and ketones. Representative examples of such solvents are tetrahydrofuran, diethyl ether, dibutyl ether, dioxane, dimethoxyethane, dimethylether of diethylene glycol, benzene, toluene, xylene, cyclopentane, cylcohexane, cycloheptane, cyclooctane, cyclododecane, methylcyclohexane, acetone, methyl ethyl ketone, diethyl ketone, dibutyl ketone and the like. Preferred solvents are tetrahydrofuran, toluene and cyclohexane.

The amount of solvent should be sufficient to dissolve all or most of the chloropolymer at reaction temperature. Generally, a stable solution is obtained using about 10-50 Kg of solvent per Kg of chloropolymer. The high molecular weight polymers are slow to dissolve so require stirring for several hours, preferably at slightly elevated temperatures of about 40°-50° C. Preferably the solvent is maintained under an inert dry nitrogen atmosphere during solvation.

The substitution reaction is conducted at moderate temperatures. A useful temperature range is about 25°-100° C. A more preferred temperature range is about 40°-70° C. The reaction is conducted until the desired degree of substitution is obtained or alternatively until the chloride content of the chloropolymer is reduced to the desired level. The reaction is usually complete in about 4-12 hours.

The amount of sodium haloalkoxide solution used should be an amount which contains sufficient sodium haloalkoxide to provide the desired degree of substitution. Generally, the solution contains about 0.9-1.1 moles of sodium haloalkoxide per equivalent of replaceable chloride in the chloropolymer.

The following examples show how the sodium haloalkoxides made according to the present process are used in a substitution reaction with chloropolymer.

EXAMPLE 4

The chloropolymer was made by placing 192.5 grams of purified polymer grade phosphonitrilic chloride cyclic trimer and a catalytic amount (0.12 wt%) of a molecular complex of $BCl_3$ and triphenyl phosphate in a clean dry polymerization tube. The tube was sealed and placed in an oven at 220° C. for 21 hours. Chloropolymer was recovered by dissolving the tubes contents in 800 ml of cyclohexane and then adding 2 liters of heptane to precipitate the high molecular weight chloropolymers while maintaining low molecular weight and cyclic chloropolymers in solution. The liquid phase was removed and discarded and the coagulated chloropolymer was washed with additional heptane. The chloropolymer was then dissolved in cyclohexane ready for use in the substitution reaction.

EXAMPLE 5

A substitution reaction was conducted by placing 749.9 grams of a sodium fluoroalkoxide solution made as in Example 3 by the addition of a dispersion of 60 grams of sodium in 90 grams of cyclohexane to a mixture of 180 grams of trifluoroethanol and 180 grams of telomer alcohol in 1450 g of tetrahydrofuran. To this was added 741.8 grams of dry tetrahydrofuran and 3.7 grams of distilled orthoallylphenol. The solution was stirred under dry nitrogen and heated to 45° C. The chloropolymer solution from Example 4 was slowly added over a 30 minute period at 45°-60° C. Stirring was continued for 8 hours at 67° C.

Work up was carried out by injecting dry carbon dioxide through the mixture to neutralize the mixture to a pH of about 6.5. Then 86 grams of 10 wt% aqueous sodium bromide was added to agglomerate the NaCl. This mixture was centrifuged and the organic liquid phase was recovered and poured into 10 liters of a heptane-hexane mixture to precipitate the polyphosphazene gum. The gum was redissolved in acetone and precipitated with 8 liters of water. The precipitated gum was dried under vacuum at 60° C. to give a fluoroalkoxide-substituted linear polyphosphazene.

We claim:

1. A process for making a sodium alkoxide of a halogen-substituted alcohol without excessive reaction of sodium with the halogen substituent, said process comprising
   (a) dispersing molten metallic sodium in a cycloalkane hydrocarbon containing about 5-8 carbon atoms at a pressure high enough to maintain said cycloalkane hydrocarbon in the liquid phase above the melting temperature of sodium;
   (b) cooling the resultant dispersion to a temperature below the melting point of sodium; and
   (c) adding about 0.9-1.0 equivalents of the resultant sodium dispersion to a solution of 1 equivalent of a halogen-substituted alcohol in an ether solvent at a temperature of about −30° C. up to reflux and at a rate such that there is not a large amount of unreacted sodium in the halogen-substituted alcohol at any time, said equivalents being based on the hydroxyl content of said halogen-substituted alcohol wherein at least a major portion of the sodium alkoxide of the halogen substituted alcohol formed is dissolved in said ether solvent.

2. A process of claim 1 wherein said cycloalkane hydrocarbon is cyclohexane.

3. A process of claim 2 wherein said ether solvent is tetrahydrofuran.

4. A process of claim 2 wherein said halogen-substituted alcohol is a fluorine-substituted alcohol.

5. A process of claim 4 wherein said ether solvent is tetrahydrofuran.

6. A process of claim 4 wherein said fluorine-substituted alcohol is a mixture of (a) trifluoroethanol and (b) a telomer alcohol which has the formula:

$$X(CF_2)_pCH_2OH$$

wherein X is selected from hydrogen and fluorine and p is an integer from 2–12 and mixtures thereof.

7. A process of claim 6 wherein said ether solvent is tetrahydrofuran.

8. A process of claim 6 wherein X is hydrogen.

9. A process of claim 4 wherein said fluorine substituted alcohol is a mixture of (a) about 30–70 wt% trifluoroethanol and (b) 70–30 wt% of a telomer alcohol having the formula:

$$X(CF_2)_pCH_2OH$$

wherein X is hydrogen or fluorine, p is an even integer from 2–12 and mixtures of such telomer alcohols.

10. A process of claim 9 wherein X is hydrogen.

11. A process of claim 10 wherein said ether solvent is tetrahydrofuran.

* * * * *